United States Patent
Jager Lezer

(12) 
(10) Patent No.: US 6,306,411 B1
(45) Date of Patent: Oct. 23, 2001

(54) COSMETIC COMPOSITION COMPRISING AN AQUEOUS DISPERSION OF FILM-FORMING POLYMER AND AN AQUEOUS SUSPENSION OF ORGANOPOLYSILOXANE

(75) Inventor: Nathalie Jager Lezer, Bourg la Reine (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/568,476

(22) Filed: May 10, 2000

(30) Foreign Application Priority Data

May 11, 1999 (FR) .................................................. 99 05999

(51) Int. Cl.$^7$ ................................. A61K 7/00; A61K 7/04; A61K 7/075; A61K 7/42

(52) U.S. Cl. .................. 424/401; 424/78.03; 424/78.02; 424/78.08; 424/70.7; 424/70.1; 424/59; 424/61; 424/63; 424/64; 524/27; 524/860; 524/862

(58) Field of Search .................... 424/78.03, 401, 424/78.08; 524/27, 377, 862, 860; 428/35.04

(56) References Cited

U.S. PATENT DOCUMENTS

| | | |
|---|---|---|
| 3,639,572 | 2/1972 | Heinrich et al. . |
| 4,423,031 | 12/1983 | Murui et al. . |
| 5,358,990 | * 10/1994 | Woodard et al. ................... 524/377 |
| 5,372,890 | * 12/1994 | Ogawa et al. ......................... 528/15 |
| 5,412,004 | * 5/1995 | Tachibana et al. ................... 524/27 |
| 5,721,026 | * 2/1998 | Feder et al. ...................... 428/35.04 |
| 5,811,487 | * 9/1998 | Schulz, Jr. et al. ................. 524/862 |
| 5,928,660 | 7/1999 | Kobayashi et al. . |

FOREIGN PATENT DOCUMENTS

| | | |
|---|---|---|
| 0 834 305 | 4/1998 | (EP) . |
| 0 855 178 | 7/1998 | (EP) . |
| 0 893 467 | 1/1999 | (EP) . |
| 10-175816 | 6/1998 | (JP) . |
| WO 98/26753 | 6/1998 | (WO) . |

* cited by examiner

Primary Examiner—Diana Dudash
Assistant Examiner—Mina Haghighatian
(74) Attorney, Agent, or Firm—Finnegan, Henderson, Farabow, Garrett & Dunner, LLP

(57) ABSTRACT

The invention relates to a composition to be applied to the skin and superficial body growths, comprising an aqueous dispersion of particles of film-forming polymer and an aqueous suspension of particles of at least partially crosslinked solid elastomeric polyorganosiloxane. The invention also relates to a process for caring for or making up keratin substances, which comprises applying the composition to the keratin substances. The composition makes it possible to obtain a film which has good staying power, is water-resistant and feels comfortable.

24 Claims, No Drawings

COSMETIC COMPOSITION COMPRISING AN AQUEOUS DISPERSION OF FILM-FORMING POLYMER AND AN AQUEOUS SUSPENSION OF ORGANOPOLYSILOXANE

The present invention relates to a composition containing an aqueous dispersion of particles of film-forming polymer and an aqueous suspension of polyorganosiloxane particles, being intended in particular for the cosmetics field. More specifically, the invention relates to a composition for caring for and making up keratin substances such as the skin, including the lips and the scalp, the nails, and the hair, including the eyelashes and the eyebrows, of human beings.

This composition can be in the form of a mascara, an eyeliner, a product for the lips, a face powder, an eyeshadow, a foundation, a make-up product for the body, a concealer product, a product for the nails, an antisun protective composition, a skin coloring composition, or a care product for the skin or superficial body growths.

Products for making up or caring for the skin or lips of human beings, such as eyeliners, foundations, or lipsticks, or alternatively for the eyelashes such as mascaras, are usually applied in the form of a thin uniform coat, leading to the formation of a film.

Make-up compositions for the skin, in particular eyeliners, or for the eyelashes, comprising an aqueous dispersion of film-forming polymer are known from U.S. Pat. Nos. 3,639,572 and 4,423,031, which are incorporated herein by reference. The film obtained with these aqueous compositions does not always have good water resistance. For example, on contact with water during bathing or taking a shower, they partially disintegrate by crumbling away or by diffusing. The crumbling and diffusion of the film gives rise to a substantial loss of intensity of the color of the make-up, obliging the consumer to freshen the application of the make-up product. Moreover, the diffusion of the film forms a highly unaesthetic aureole around the made-up region (in particular the eyes). Tears and perspiration also give rise to these same drawbacks. This is especially the case for an eyeliner.

Furthermore, these compositions also have the drawback of transferring, i.e. of becoming at least partly deposited, leaving marks on certain supports with which they may come into contact, in particular a fabric (clothing, towels, handkerchiefs), the skin (fingers) or a glass, a cup or a cigarette as regards the products for the lips. This results in a decrease, or even disappearance, of the make-up, thus making it necessary to freshen the application of the make-up composition regularly. Moreover, the appearance of unacceptable marks, in particular on shirt collars, can inhibit certain women from using this type of make-up.

In addition, the film obtained with these compositions may have a coarse feel or may not be sufficiently flexible, leaving the user with a sensation of discomfort and inconvenience.

The aim of the present invention is to provide a make-up or care composition for keratin substances that is easily applied and can give a film, which has good staying power and water resistance and which feels comfortable.

The inventors have discovered that the use of an aqueous suspension of particles of solid elastomeric polyorganosiloxane in a composition comprising an aqueous dispersion of particles of film-forming polymer makes it possible to obtain a composition which leads to the formation of a film that is entirely water-resistant. The film obtained also has transfer-resistance properties and has a matt appearance, thus giving the composition matt-effect properties. The composition feels comfortable to apply, spreads well and has a soft, non-sticky feel.

More specifically, a subject of the present invention is a composition to be applied to the skin and superficial body growths, comprising an aqueous dispersion of particles of film-forming polymer, characterized in that it further comprises an aqueous suspension of particles of at least partially crosslinked solid elastomeric polyorganosiloxane.

A subject of the invention is also a cosmetic process for the making up or for the non-therapeutic treatment of keratin substances, comprising applying a composition as defined above to the keratin substances.

A subject of the invention is also the use, in a cosmetic composition or for the manufacture of a topical composition, of an aqueous dispersion of film-forming polymer and of an aqueous suspension of solid particles of at least partially crosslinked elastomeric polyorganosiloxane, in order to obtain a film that is water-resistant and/or does not transfer and/or feels comfortable and/or gives a matt effect.

The term "elastomeric" refers to a flexible, deformable material that has viscoelastic properties, including the consistency of a sponge or flexible sphere. Its modulus of elasticity is such that this material withstands deformation and has a limited capacity for extension and contraction. This material is capable of regaining its original shape after having been stretched. This elastomer is formed from high molecular weight polymeric chains whose mobility is limited by a network of crosslinking points.

The elastomeric polyorganosiloxanes in accordance with the invention are partially or totally crosslinked, of three-dimensional structure, and in the form of powder suspended in water.

The elastomeric polyorganosiloxanes according to the invention can be chosen from the crosslinked polymers described in patent application JP-A-10/175 816 and U.S. Pat. No. 5,928,660, which are incorporated herein by reference. According to the patent, they are obtained by addition reaction and crosslinking in the presence of a catalyst, especially of the platinum type, of at least:

(a) one polyorganosiloxane (i) containing at least two vinyl groups in position $\alpha$, $\omega$ of the silicone chain per molecule; and (b) one organosiloxane (ii) containing at least one hydrogen atom linked to a silicon atom per molecule.

In particular, the polyorganosiloxane (i) may be chosen from polydimethylsiloxanes and is more specifically an $\alpha$, $\omega$-dimethylvinylpolydimethylsiloxane.

The elastomeric polyorganosiloxanes in the composition according to the invention are in the form of an aqueous suspension. This suspension can be obtained in particular as follows:

(a) mixing the polyorganosiloxane (i) and the organosiloxane (ii);
(b) adding the aqueous phase containing an emulsifier to the mixture from step (a);
(c) emulsifying the aqueous phase and the said mixture;
(d) adding hot water to the emulsion from phase (c); and
(e) polymerizing the polyorganosiloxane (i) and the organosiloxane (ii) of the emulsion in the presence of a platinum catalyst.

The water of step (d) is advantageously added at a temperature of 40–60° C. After step (e), it is possible to dry the particles obtained, in order to evaporate therefrom all or some of the water trapped.

The polyorganosiloxanes in the composition of the invention are, for example, those sold under the names BY 29-122 and BY 29-119 by the company Dow-Corning Toray. A mixture of these commercial products can also be used.

Preferably, the elastomeric polyorganosiloxane powder is present in the composition in a solids content ranging from about 0.5 to about 65% by weight, relative to the total weight of the composition, more preferably from about 3 to about 45% by weight, and better still from about 5% to about 30% by weight, and in any case in an amount, which is sufficient to increase the water-resistance of the composition.

Preferably, the particles of elastomeric polyorganosiloxane (as active material) can have a size ranging from about 0.1 to about 500 μm and better still from about 3 to about 200 μm. These particles can be spherical, flat, or amorphous, but preferably have a spherical shape.

According to the invention, the polyorganosiloxane particles are present in the composition in the form of an aqueous suspension; they are thus directly in suspension in the water. This water can be added to any composition, irrespective of its pharmaceutical form.

In order to be suspended stably in the water, these polyorganosiloxane particles can be combined with one or more nonionic, cationic, or anionic surfactants with an HLB≧8. Preferably, step (c) is performed in the presence of a nonionic surfactant.

The proportion of surfactants is preferably from about 0.1 to about 20 parts by weight per 100 parts by weight of the elastomeric polyorganosiloxane suspension, and better still from about 0.5 to about 10 parts by weight (cf. description in document JP-A-10/175 816).

The composition according to the invention also contains a film-forming polymer in the form of particles in aqueous dispersion, which is generally known as a latex or pseudolatex.

In the present patent application, the expression "film-forming polymer" means a polymer capable of forming, by itself or in the presence of a film-forming auxiliary agent, an isolable film.

Among the film-forming polymers, which can be used in the composition of the present invention, mention may be made of synthetic polymers (of radical-mediated type or of polycondensate type), polymers of natural origin, and mixtures thereof.

The expression "radical-mediated film-forming polymer" means a polymer obtained by polymerization of unsaturated monomers, in particular ethylenic monomers, each monomer being capable of homopolymerizing (unlike the polycondensates).

The film-forming polymers of radical-mediated type can in particular be vinyl polymers or copolymers, in particular acrylic polymers.

The vinyl film-forming polymers can result from the polymerization of ethylenic monomers having at least one acid group and/or esters of these acidic monomers and/or amides of these acidic monomers.

Anionic radical-mediated film-forming polymers are preferably used, i.e. polymers having at least one monomer containing an acidic group.

Monomers bearing an acidic group, which can be used, are α, β-ethylenic unsaturated carboxylic acids such as acrylic acid, methacrylic acid, crotonic acid, maleic acid, or itaconic acid. (Meth)acrylic acid and crotonic acid are preferably used, and more preferably (meth)acrylic acid.

The esters of acidic monomers are advantageously chosen from (meth)acrylic acid esters (also referred to as (meth) acrylates), in particular alkyl (meth)acrylates in particular of $C_1$–$C_{20}$ alkyl, preferably of $C_1$–$C_8$ alkyl, aryl (meth) acrylates in particular of $C_6$–$C_{10}$ aryl, and hydroxyalkyl (meth)acrylates in particular of $C_2$–$C_6$ hydroxyalkyl.

Among the alkyl (meth)acrylates, which may be mentioned, are methyl methacrylate, ethyl methacrylate, butyl methacrylate, isobutyl methacrylate, 2-ethylhexyl methacrylate, and lauryl methacrylate.

Among the hydroxyalkyl (meth)acrylates, which may be mentioned, are hydroxyethyl acrylate, 2-hydroxypropyl acrylate, hydroxyethyl methacrylate, and 2-hydroxypropyl methacrylate.

Among the aryl (meth)acrylates, which may be mentioned, are benzyl acrylate and phenyl acrylate.

The (meth)acrylic acid esters, which are particularly preferred, are the alkyl (meth)acrylates.

According to the invention, the alkyl group of the esters can be either fluorinated or perfluorinated, i.e., some or all of the hydrogen atoms in the alkyl group are replaced with fluorine atoms.

Amides of the acidic monomers, which may be mentioned, for example, are (meth)acrylamides, and in particular N-alkyl(meth)acrylamides in particular of $C_2$–$C_{12}$ alkyl. Among the N-alkyl(meth)acrylamides which may be mentioned are N-ethylacrylamide, N-t-butylacrylamide and N-t-octylacrylamide.

The vinyl film-forming polymers can also result from the homopolymerization or copolymerization of monomers chosen from vinyl esters and styrene monomers. In particular, these monomers can be polymerized with acidic monomers and/or their esters and/or their amides, such as those mentioned above.

Examples of vinyl esters, which may be mentioned, are vinyl acetate, vinyl neodecanoate, vinyl pivalate, vinyl benzoate, and vinyl t-butylbenzoate.

Styrene monomers, which may be mentioned, are styrene and α- methylstyrene.

The list of monomers given is not limiting, and it is possible to use any monomer known to those skilled in the art that falls into the categories of acrylic and vinyl monomers (including monomers modified with a silicone chain).

As acrylic film-forming polymers, which can be used according to the invention, mention may be made of those sold under the names Neocryl XK-90®, Neocryl A-1070®, Neocryl A-1090®, Neocryl BT-62®, Neocryl A-1079®, and Neocryl A-523® by the company Zeneca, and Dow Latex 432® by the company Dow Chemical.

Among the film-forming polycondensates, mention may also be made of polyurethanes, polyesters, polyesteramides, polyesters containing a fatty chain, polyamides, and epoxy ester resins.

The polyurethanes can be chosen from anionic, cationic, nonionic, or amphoteric polyurethanes, polyurethane-acrylics, polyurethane-polyvinylpyrrolidones, polyester-polyurethanes, polyether-polyurethanes, polyureas, polyurea-polyurethanes, and mixtures thereof.

The film-forming polyurethane can be, for example, an aliphatic, cycloaliphatic, or aromatic polyurethane, polyurea-urethane, or polyurea copolymer, comprising, alone or as a mixture:

at least one sequence of aliphatic and/or cycloaliphatic and/or aromatic polyester origin, and/or at least one branched or unbranched silicone sequence, for example polydimethylsiloxane or polymethylphenylsiloxane, and/or at least one sequence comprising fluorinated groups.

The film-forming polyurethanes as defined in the invention can also be obtained from branched or unbranched polyesters, or from alkyds comprising labile hydrogens, which are modified by reaction with a diisocyanate and a bifunctional (for example dihydro, diamino or hydroxyamino) organic compound also comprising either a carboxylic acid or carboxylate group, or a sulphonic acid or sulphonate group, or alternatively a neutralizable tertiary amine group or a quaternary ammonium group.

As film-forming polyurethanes which can be used according to the invention, use may be made of those sold under the names Neorez R-981® and Neorez R-974® by the company Zeneca, Avalure UR-405®, Avalure UR-41 0®, Avalure UR-425®, Avalure UR-450®, Sancure 875®, Sancure 861®, Sancure 878®, and Sancure 2060® by the company Goodrich, Impranil 85® by the company Bayer, and Aquamere H-1511® by the company Hydromer.

The polyesters can be obtained, in a known manner, by polycondensation of dicarboxylic acids with polyols, in particular diols.

The dicarboxylic acid can be aliphatic, alicyclic, or aromatic. Examples of such acids, which may be mentioned, are: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid, and 2,6-naphthalenedicarboxylic acid. These dicarboxylic acid monomers can be used alone or in combinations of at least two dicarboxylic acid monomers. Among these monomers, the ones preferably chosen are phthalic acid, isophthalic acid, and terephthalic acid.

The diol can be chosen from aliphatic, alicyclic, and aromatic diols. The diol preferably used is one chosen from: ethylene glycol, diethylene glycol, triethylene glycol, 1,3-propanediol, cyclohexanedimethanol, and 1,4-butanediol. Other polyols, which can be used, are glycerol, pentaerythritol, sorbitol, and trimethylolpropane.

The polyesteramides can be obtained in a similar manner to that for the polyesters, by polycondensation of diacids with either diamines or amino alcohols. Diamines, which can be used, are ethylenediamine, hexamethylenediamine, and meta- or para-phenylenediamine. An amino alcohol, which can be used, is monoethanolamine.

The polyester can also comprise at least one monomer bearing at least one —$SO_3M$ group, with M representing a hydrogen atom, an ammonium ion $NH_4^+$, or a metal ion such as, for example, an $Na^+$, $Li^+$, $K^+$, $Mg^{2+}$, $Ca^{2+}$, $Cu^{2+}$, $Fe^{2+}$, or $Fe^{3+}$ ion. A difunctional aromatic monomer comprising such a —$SO_3M$ group can be used in particular.

The aromatic nucleus of the bifunctional aromatic monomer also bearing a —$SO_3M$ group as described above can be chosen, for example, from benzene, naphthalene, anthracene, biphenyl, oxybiphenyl, sulphonylbiphenyl, and methylenebiphenyl nuclei. Examples of bifunctional aromatic monomers also bearing a —$SO_3M$ group, which may be mentioned, are: sulphoisophthalic acid, sulphoterephthalic acid, sulphophthalic acid, and 4-sulphonaphthalene-2,7-dicarboxylic acid.

Copolymers based on isophthalate/sulphoisophthalate, and more particularly copolymers obtained by condensation of diethylene glycol, cyclohexanedimethanol, isophthalic acid, and sulphoisophthalic acid, are preferably used in the compositions that form the subject of the invention. Such polymers are sold, for example, under the brand name Eastman AQ by the company Eastman Chemical Products.

The polyesters can in particular comprise a monomer bearing a chromophore, such as those described in patent application WO 98/26753, which is incorporated herein by reference.

The polymers of natural origin, which are optionally modified, can be chosen from shellac resin, sandarac gum, dammar resins, elemi gums, copal resins, water-insoluble cellulose polymers and mixtures thereof.

Mention may also be made of polymers resulting from the radical-mediated polymerization of one or more radical monomers inside and/or partially at the surface of pre-existing particles of at least one polymer chosen from the group consisting of polyurethanes, polyureas, polyesters, polyesteramides and alkyds. These polymers are generally referred to as hybrid polymers.

The dispersion comprising one or more film-forming polymers can be prepared by a person skilled in the art on the basis of his general knowledge.

Preferably, the size of the polymer particles in aqueous dispersion can range from about 10 to about 500 nm and more preferably from about 20 to about 300 nm.

Preferably, the film-forming polymer in aqueous dispersion can be present in the composition according to the invention in a solids content ranging from about 0.1% to about 60% by weight relative to the total weight of the composition, more preferably from about 0.1% to about 40% by weight, and better still from about 0.1% to about 20% by weight. The addition of the elastomeric polyorganosiloxane makes it possible in particular to appreciably increase the water-resistance of a composition having a small content of latex or pseudolatex (i.e. less than 30%, or even less than 10%, by weight of film-forming polymeric solids relative to the total weight of the composition).

The composition according to the invention can comprise a film-forming auxiliary agent, which promotes the formation of a film with the particles of the film-forming polymer. Such film-forming agents can be chosen from any compounds known to those skilled in the art as being capable of satisfying the desired function, and can be chosen in particular from plasticizers and coalescence agents.

The aqueous medium (or aqueous phase) of the composition can consist essentially of water. Alternatively, it can comprise a mixture of water and water-miscible miscible solvents such as lower monoalcohols containing from 1 to 5 carbon atoms, glycols containing from 2 to 8 carbon atoms, $C_3$–$C_4$ ketones, and $C_2$–$C_4$ aldehydes. In practice, the aqueous medium represents from about 5% to about 99.4% by weight relative to the total weight of the composition.

The composition can also comprise at least one dyestuff, such as pulverulent compounds, water-soluble dyes, and/or liposoluble dyes, in a proportion of from about 0.01 to about 50% of the total weight of the composition. The pulverulent compounds can be chosen from the pigments and/or nacres and/or fillers usually used in cosmetic or dermatological compositions. Preferably, the pulverulent compounds represent from about 0.1 to about 25% of the total weight of the composition and better still from about 1 to about 20%.

The pigments can be white or colored, and inorganic and/or organic. Among the inorganic pigments, which may be mentioned, are titanium dioxide, optionally surface-treated, zirconium oxide, or cerium oxide, as well as iron oxide, chromium oxide, manganese violet, ultramarine blue, chromium hydrate, and ferric blue. Among the organic pigments, which may be mentioned, are carbon black, pigments of D&C type, and lakes based on cochineal carmine, barium, strontium, calcium, or aluminum.

The nacreous pigments can be chosen from white nacreous pigments, such as mica coated with titanium or with bismuth oxychloride; colored nacreous pigments such as titanium mica with iron oxides, titanium mica with, in particular, ferric blue or chromium oxide, titanium mica with an organic pigment of the abovementioned type; and nacreous pigments based on bismuth oxychloride.

The fillers can be chosen from those, which are well known to those skilled in the art and which are commonly used in cosmetic compositions.

Among the water-soluble dyes, which may be mentioned, are the disodium salt of ponceau, the disodium salt of alizarin green, quinoline yellow, the trisodium salt of amaranth, the disodium salt of tartrazine, the monosodium salt of rhodamine, the disodium salt of fuchsin, xanthophyll, and mixtures thereof.

Among the liposoluble dyes, which may be mentioned, are Sudan red, DC Red 17, DC Green 6, β-carotene, soybean oil, Sudan brown, DC Yellow 11, DC Violet 2, DC Orange 5, and quinoline yellow.

The composition can also comprise one or more active agents, in particular cosmetic or dermatological active agents, such as moisturizers, vitamins, essential fatty acids, proteins, ceramides, sunscreens, free-radical scavengers, or anti-inflammatory agents. Needless to say, a person skilled in the art will take care to select the optional additional compound(s) and/or the amount(s) thereof, such that the advantageous properties of the composition for the use according to the invention are not, or are not substantially, adversely affected by the addition envisaged. These active agents can be used, for example, in a content ranging from about 0.001% to about 20% by weight relative to the total weight of the composition.

Depending on the type of application envisaged, the composition according to the invention can also comprise the constituents conventionally used in the fields under consideration, which are present in an amount which is suitable for the desired pharmaceutical form.

The composition can also contain any additive usually used in such compositions, such as thickeners, fragrances, preserving agents, surfactants in addition to those in the polyorganosiloxane suspension, oils, waxes, and antioxidants.

Advantageously, the composition of the invention can contain one or more aqueous-phase gelling agents as additives. Among the aqueous-phase gelling agents, which can be used according to the invention, mention may be made of water-soluble cellulosic gelling agents, such as hydroxyethylcellulose, methylcellulose, hydroxypropylcellulose and carboxymethylcellulose; guar gum; quaternized guar gum; nonionic guar gums comprising $C_1$–$C_6$ hydroxyalkyl groups; xanthan gum; carob gum; scleroglucan gum; gellan gum; rhamsan gum or karaya gum; alginates, maltodextrin, and starch and its derivatives; hyaluronic acid and its salts; clays and in particular montmorillonites, hectorites or bentones, and laponites; polymers containing a carboxylic group, such as at least partially neutralized, crosslinked polyacrylic acids, such as the "Carbopol" or "Carbomer" products from the company Goodrich (for example Carbomer 980 neutralized with triethanolamine - abbreviated as TEA); polyglyceryl (meth)acrylate polymers; polyvinylpyrrolidone; polyvinyl alcohol; crosslinked acrylamide polymers and copolymers; crosslinked methacryloyloxyethyltrimethylammonium chloride homopolymers; and associated polyurethanes.

According to the invention, the aqueous-phase gelling agent is preferably chosen from xanthan gum, clays (bentone or laponite), associative polyurethanes, cellulosic thickeners in particular hydroxyethylcellulose, and at least partially neutralized, crosslinked polyacrylic acids.

The composition can be in the form of a gel, a lotion, a stick, a water-in-oil, oil-in-water, wax-in-water or water-in-wax emulsion, a multiple emulsion, or a vesicular dispersion containing ionic and/or nonionic lipids.

These compositions for topical application can in particular constitute a cosmetic, dermatological, hygiene, or pharmaceutical composition for protecting, caring for, or treating the skin in particular for the face, for the neck, for the hands, or for the body (for example a care cream, an antisun gel or a body gel), a make-up composition, an antisun protective composition, or an artificial tanning composition.

The make-up composition can be, in particular, a mascara, an eyeliner, a product for the lips (lipstick), an eyeshadow, a face powder, a concealer product, a foundation, a product for the nails (nail varnish or care base), or a make-up product for the body such as a temporary or semi-permanent tattoo.

The invention is illustrated in greater detail in the examples which follow.

EXAMPLES 1 to 8

Four eyeshadows according to the invention (Examples 1 to 4) and four eyeshadows not forming part of the invention (Examples 5 to 8), having the compositions below, were prepared:

EXAMPLES 1 to 4

| | |
|---|---|
| Polyorganosiloxane as an aqueous suspension containing 63% solids (BY29-119 from the company Dow Corning) | 20.16 g AM |
| Hydroxypropylcellulose | 2 g |
| Film-forming polymer as an aqueous dispersion | 2.45 g AM |
| Glycerol | 1 g |
| Nacre | 5 g |
| Water | qs 100 g |

EXAMPLES 5 to 8 (Comparative)

| | |
|---|---|
| Hydroxypropylcellulose | 2 g |
| Film-forming polymer as an aqueous dispersion | 2.45 g AM |
| Glycerol | 1 g |
| Nacre | 5 g |
| Water | qs 100 g |

The aqueous dispersions of film-forming polymer below were used:

EXAMPLES 1 and 5
Polyvinylpyrrolidone Copolymer Containing 15% AM (Aquamere H-1511 From the Company Hydromer)

EXAMPLES 2 and 6
Acrylic Copolymer Containing 60% AM (Neocryl A-523 From the Company Zeneca)

EXAMPLES 3 and 7
Polyurethane Containing 49% AM (Avalure UR-425 From the Company Goodrich)

EXAMPLES 4 and 8
Polyurethane-polyether Containing 27% AM (Sancure 2060 From the Company Goodrich)

For each composition, a layer 200 µm thick before drying was applied to a glass plate and was then left to dry for one hour at room temperature. A trickle of water was run onto the dry film and the time (in seconds) required for the film to start degrading was measured.

The results below were obtained:

| Example | Time |
|---------|------|
| 1 | 240 |
| 5 | 70 |
| 2 | 180 |
| 6 | 90 |
| 3 | 70 |
| 7 | 30 |
| 4 | 60 |
| 8 | 25 |

It is found that the films of Examples 1 to 4 according to the invention have better water-resistance than the films of Examples 5 to 8 not containing the polyorganosiloxane in aqueous suspension.

What is claimed is:

1. A composition to be applied to the skin and superficial body growths, comprising an aqueous dispersion of particles of film-forming polymer and an aqueous suspension of particles of at least partially crosslinked solid elastomeric polyorganosiloxane.

2. The composition according to claim 1, wherein the elastomeric polyorganosiloxane is obtained by addition reaction and crosslinking, in the presence of a catalyst, of at least:
   (a) one polyorganosiloxane (i) containing at least two vinyl groups in position $\alpha,\omega$ of the silicone chain per molecule; and
   (b) one organosiloxane (ii) containing at least one hydrogen atom linked to a silicon atom per molecule.

3. The composition according to claim 2, wherein the polyorganosiloxane (i) is chosen from polydimethylsiloxanes.

4. The composition according to claim 1, wherein the polyorganosiloxane is an $\alpha,\omega$-dimethylvinylpolydimethylsiloxane.

5. The composition according to claim 2, wherein the aqueous suspension of particles of elastomeric polyorganosiloxane is obtained by the method comprising the steps of:
   (a) mixing the polyorganosiloxane (i) and the organosiloxane (ii);
   (b) adding an aqueous phase containing an emulsifier to the mixture from step (a);
   (c) emulsifying the aqueous phase and the said mixture;
   (d) adding hot water to the emulsion from phase (c); and
   (e) polymerizing the polyorganosiloxane (i) and the organosiloxane (ii) of the emulsion in the presence of a platinum catalyst.

6. The composition according to claim 5, wherein step (c) is carried out in the presence of a nonionic surfactant.

7. The composition according to claim 1, wherein the size of the particles of elastomeric polyorganosiloxane range from about 0.1 to about 500 $\mu$m.

8. The composition according to claim 1, wherein the size of the particles of elastomeric polyorganosiloxane range from about 3 to about 200 $\mu$m.

9. The composition according to claim 1, wherein the solids content of the elastomeric polyorganosiloxane ranges from about 0.5% to about 65% by weight relative to the total weight of the composition.

10. The composition according to claim 1, wherein the solids content of the elastomeric polyorganosiloxane ranges from about 3% to about 45% by weight relative to the total weight of the composition.

11. The composition according to claim 1, wherein the film-forming polymer is selected from radical polymers, polycondensates, polymers of natural origin, and mixtures thereof.

12. The composition according to claim 1, wherein the film-forming polymer is selected from vinyl polymers, polyurethanes, and polyesters.

13. The composition according to claim 1, wherein the solids content of the film-forming polymer ranges from about 0.1% to about 60% by weight relative to the total weight of the composition.

14. The composition according to claim 1, wherein the solids content of the film-forming polymer ranges from about 0.1% to about 40% by weight relative to the total weight of the composition.

15. The composition according to claim 1, wherein the size of the particles of film-forming polymer range from about 10 to about 500 nm.

16. The composition according to claim 1, wherein the size of the particles of film-forming polymer range from about 20 to about 300 nm.

17. The composition according to claim 1, wherein the composition further comprises at least one water-miscible solvent.

18. The composition according to claim 17, wherein the water-miscible solvent is selected from lower monoalcohols containing from 1 to 5 carbon atoms, glycols containing from 2 to 8 carbon atoms, $C_3$–$C_4$ ketones, and $C_2$–$C_4$ aldehydes.

19. The composition according to claim 1, wherein the composition further comprises at least one additive selected from thickeners, fragrances, preserving agents, surfactants other than those in the suspension of polyorganosiloxanes, oils, waxes, plasticizers, coalescence agents, dyestuffs, fillers, antioxidants, and cosmetic or dermatological active agents.

20. The composition according to claim 1, wherein the composition is in the form of a mascara, an eyeliner, a product for the lips, an eyeshadow, a face powder, a concealer product, a foundation, a make-up product for the body, a product for the nails, a product for caring for or treating keratin substances, an antisun protective composition, or an artificial tanning composition.

21. A method for the making up of a keratin substance comprising the application of a composition according to claim 1 to the keratin substance.

22. A method for the non-therapeutic treatment of a keratin substance comprising the application of a composition according to claim 1 to the keratin substance.

23. A method for the manufacture of a cosmetic composition comprising the inclusion of a composition according to claim 1 in the cosmetic composition.

24. A method for the manufacture of a topical composition comprising the inclusion of a composition according to claim 1 in the topical composition.

* * * * *